United States Patent
Tobias

(10) Patent No.: US 8,312,758 B2
(45) Date of Patent: Nov. 20, 2012

(54) APPARATUS AND METHOD FOR USING THE SPEED OF SOUND IN PHOTOACOUSTIC GAS SENSOR MEASUREMENTS

(75) Inventor: Peter Tobias, Minneapolis, MN (US)

(73) Assignee: Honeywell International Inc., Morristwon, NJ (US)

( * ) Notice: Subject to any disclaimer, the term of this patent is extended or adjusted under 35 U.S.C. 154(b) by 566 days.

(21) Appl. No.: 12/333,056

(22) Filed: Dec. 11, 2008

(65) Prior Publication Data

US 2010/0147051 A1 Jun. 17, 2010

(51) Int. Cl.
*G01N 21/59* (2006.01)

(52) U.S. Cl. ........................................ 73/24.02

(58) Field of Classification Search ............ None
See application file for complete search history.

(56) References Cited

U.S. PATENT DOCUMENTS

| | | | |
|---|---|---|---|
| 4,163,382 A * | 8/1979 | Amer | 73/24.02 |
| 4,557,603 A | 12/1985 | Oehler et al. | |
| 4,740,086 A | 4/1988 | Oehler et al. | |
| 4,818,882 A | 4/1989 | Nexo et al. | |
| 4,866,681 A | 9/1989 | Fertig | |
| 5,933,245 A | 8/1999 | Wood et al. | |
| 6,608,683 B1 * | 8/2003 | Pilgrim et al. | 356/432 |
| 6,853,449 B2 | 2/2005 | Hocker | |
| 2007/0045128 A1 | 3/2007 | Krafthefer et al. | |
| 2007/0139165 A1 | 6/2007 | Liu | |
| 2008/0011055 A1 * | 1/2008 | Riddle | 73/24.02 |
| 2008/0282765 A1 | 11/2008 | Bonne et al. | |

OTHER PUBLICATIONS

Benedetto, R.M., Gavioso, R. Spagnolo. Measurement of speed of sound in gas-filled acoustic resonator. IEEE Instrumentation and Measurement Technology Conference. Brussels, Belgium. 1996.*

* cited by examiner

*Primary Examiner* — Hezron E Williams
*Assistant Examiner* — Mark A Shabman

(57) ABSTRACT

A photoacoustic gas sensor includes a photoacoustic cell configured to receive a gas mixture having a first gas component and a second gas component. The photoacoustic gas sensor also includes a light source configured to provide light to the photoacoustic cell. The photoacoustic gas sensor further includes a photoacoustic cell controller configured to measure a concentration of the second gas component using a speed of sound through the gas mixture, where the speed of sound is determined based on an absorption associated with the first gas component. In addition, the photoacoustic gas sensor could include a temperature sensor configured to measure a temperature of the gas mixture, where the photoacoustic cell controller is configured to determine the concentration of the second gas component using the speed of sound and the temperature.

21 Claims, 5 Drawing Sheets

APPARATUS AND METHOD FOR USING THE SPEED OF SOUND IN PHOTOACOUSTIC GAS SENSOR MEASUREMENTS

TECHNICAL FIELD

This disclosure is directed generally to photoacoustic gas sensors and, in particular, to an apparatus and method for using the speed of sound in photoacoustic gas sensor measurements.

BACKGROUND

A photoacoustic gas sensor may be used to detect a concentration level of a gas component in a gas sample. In photoacoustic gas sensors, a gas mixture is illuminated with light that has a certain wavelength or range of wavelengths. A target gas component of the gas mixture absorbs the light and increases the temperature of the gas mixture. The increase in temperature of the gas mixture increases the pressure of the gas mixture. The increase in pressure of the gas mixture due to the temperature increase can be measured. A microphone can be used to detect and measure the increase in pressure of the gas mixture.

A higher concentration of the target gas component in the gas mixture will cause a higher increase in the pressure of the gas mixture. This higher increase in the pressure of the gas mixture causes the detecting microphone to record a louder sound.

A conventional photoacoustic gas sensor 100 in resonance mode is illustrated in FIG. 1. A light source 110 (such as a light bulb or laser) generates modulated light 120 of a certain wavelength. The amplitude of the light is modulated, e.g., with a square wave with ON and OFF states. The light 120 enters a photoacoustic cell 130 (also referred to as a photoacoustic gas sensor chamber 130) through a transparent or translucent wall 140. The light amplitude modulation frequency should be the same as the resonance frequency of the sound wave in the photoacoustic cell 130.

The opposite wall of the photoacoustic cell 130 comprises an opaque wall 150 or a mirror 150. In the embodiment shown in FIG. 1, the photoacoustic cell 130 is in the shape of a cylinder. A microphone 160 is associated with and is in acoustic contact with the interior of the photoacoustic cell 130. The microphone 160 detects the pressure within the photoacoustic cell 130.

It is important that the light illuminate only a portion (and not all) of the photoacoustic cell 130. The resonance frequency corresponds to a standing wave with nodes and anti-nodes of the sound pressure. The nodes are surfaces within the cell 130 and the anti-nodes are the spaces between the surfaces. The pressure at the nodes is constant, and the pressure in an anti-node at a given time is either increasing or decreasing (except for two points during the cycle when the pressure is not changing at any point).

For a cylindrically shaped cell 130 of the type that is shown in FIG. 1 there will be a standing sound wave along the symmetry axis. The pressure node 195 is the plane in the middle of the cell 130 between the two flat ends of the cell 130. One anti-node is located to the right of the pressure node 195 in the cell 130. The other anti-node is located to the left of the pressure node 195. The modulated light should illuminate only an anti-node if the pressure is increasing to introduce more energy into the standing wave and make the pressure variations greater.

For a cylindrically shaped cell 130 of the type that is shown in FIG. 1 this means that only one half of the cell 130 is illuminated with modulated light. During the time when the modulated light is on, the pressure in the illuminated portion of the cell 130 increases. During the time when the modulated light is off, the pressure in the previously illuminated portion of the cell 130 decreases. The other (non-illuminated) portion of the cell 130 is present to complete the resonance space of the cell 130.

The output of the microphone 160 is provided to an amplifier 170. The amplifier 170 amplifies the output signal of the microphone 160 and provides the amplified output to an analog-to-digital converter 180. The analog-to-digital converter 180 converts the amplified analog signal to a digital signal and provides the digital signal to a controller 190. The modulation signal of the light source 110 is either generated in the controller 190 and sent to the light source 110 or generated near the light source 110 and sent to the controller 190. The controller 190 uses the digital signal and the modulation signal to determine the concentration level of the target gas component that is in the mixture of gases within the photoacoustic cell 130.

In the analysis of a gas mixture, it is often useful to have many independent measurements of the gas mixture. It is also often useful to determine a concentration of a second target gas component in a mixture of gases in which the concentration of a first target gas component has already been measured. In conventional photoacoustic gas sensors, a concentration of a second target gas component is determined using a second light source that generates light with a wavelength that is absorbed by the second target gas component. This technique requires the use of a second light source.

SUMMARY

This disclosure provides an apparatus and method for using the speed of sound in photoacoustic gas sensor measurements.

In a first embodiment, a photoacoustic gas sensor includes a photoacoustic cell configured to receive a gas mixture. The photoacoustic gas sensor also includes a light source configured to provide modulated light to the photoacoustic cell which is absorbed by at least one gas component in the gas mixture. The photoacoustic gas sensor further includes a photoacoustic cell controller configured to calculate pressure variations resulting from the light absorption and a speed of sound through the gas mixture, where the speed of sound is determined based on the light absorption. The photoacoustic gas sensor is also configured to determine the composition of the gas mixture from the pressure variations and the speed of sound.

In particular embodiments, the gas mixture comprises a first gas component and a second gas component and a third gas component for balance. The photoacoustic cell controller is also configured to measure concentration of the three gas components using the pressure variations and the speed of sound through the gas mixture, where the speed of sound determined based on an absorption associated with the first gas component.

In other particular embodiments, the photoacoustic cell controller is also configured to determine the speed of sound through the gas mixture using at least one resonance of the photoacoustic cell. The photoacoustic cell controller may be further configured to determine the speed of sound using a relationship between a resonance frequency of the photoacoustic cell and a wavelength or wavelength range of the light.

In yet other particular embodiments, the photoacoustic gas sensor also includes a temperature sensor configured to measure a temperature of the gas mixture. The photoacoustic cell controller is configured to determine the composition of the gas mixture using the speed of sound and the temperature and the concentrations of the absorbing gases.

In still other particular embodiments, the photoacoustic cell controller is configured to determine the composition of the gas mixture using a relationship of:

$$\text{Speed of sound} = \sqrt{f(c1, c2, \ldots, T)kT}$$

where k represents the Boltzmann constant, T represents an absolute temperature of the gas mixture in Kelvins, and f(c1, c2, ..., T) is a predetermined function of T and the gas composition with different concentrations (c1, c2, ...).

In other particular embodiments, the photoacoustic cell controller is further configured to control the light source in order to lock a frequency of the light to a resonance associated with the photoacoustic cell.

In additional particular embodiments, the light has a first wavelength or wavelength range and is absorbed by the first gas component. Also, the photoacoustic cell controller is configured to determine the concentration of the second gas component without any measurements taken using light having a second wavelength or wavelength range that is absorbed by the second gas component.

In a second embodiment, a photoacoustic cell controller includes a speed of sound determination module configured to determine a speed of sound through a gas mixture in a photoacoustic cell using an absorption of a first gas component in the gas mixture. The photoacoustic cell controller also includes a gas concentration determination module configured to determine a concentration of a second gas component using the speed of sound through the gas mixture.

In a third embodiment, a method of operating a photoacoustic gas sensor that comprises a photoacoustic cell includes determining a speed of sound through a gas mixture in the photoacoustic cell using an absorption of a first gas component in the gas mixture. The method also includes determining a concentration of at least one other gas component of the gas mixture using the speed of sound through the gas mixture.

Other technical features may be readily apparent to one skilled in the art from the following figures, descriptions, and claims.

BRIEF DESCRIPTION OF THE DRAWINGS

For a more complete understanding of this disclosure and its advantages, reference is now made to the following descriptions taken in conjunction with the accompanying drawings, in which.

DETAILED DESCRIPTION

FIGS. 2 through 5 and the various embodiments used to describe the principles of the present invention in this patent document are by way of illustration only and should not be construed in any way to limit the scope of the invention. Those skilled in the art will understand that the principles of the invention may be implemented in any type of suitably arranged photoacoustic gas sensor.

Figure 1:
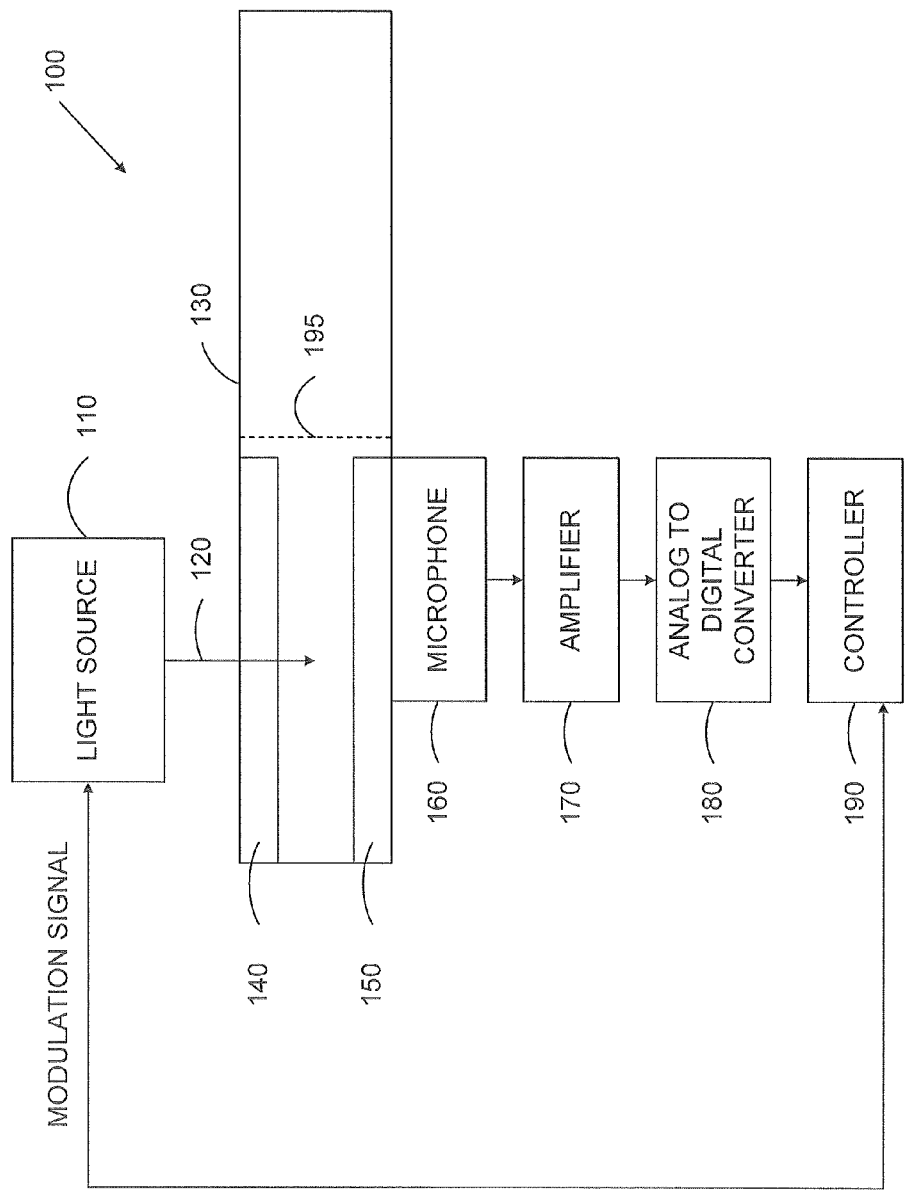
FIG. 1 illustrates a conventional photoacoustic gas sensor in resonance mode.
Figure 2:
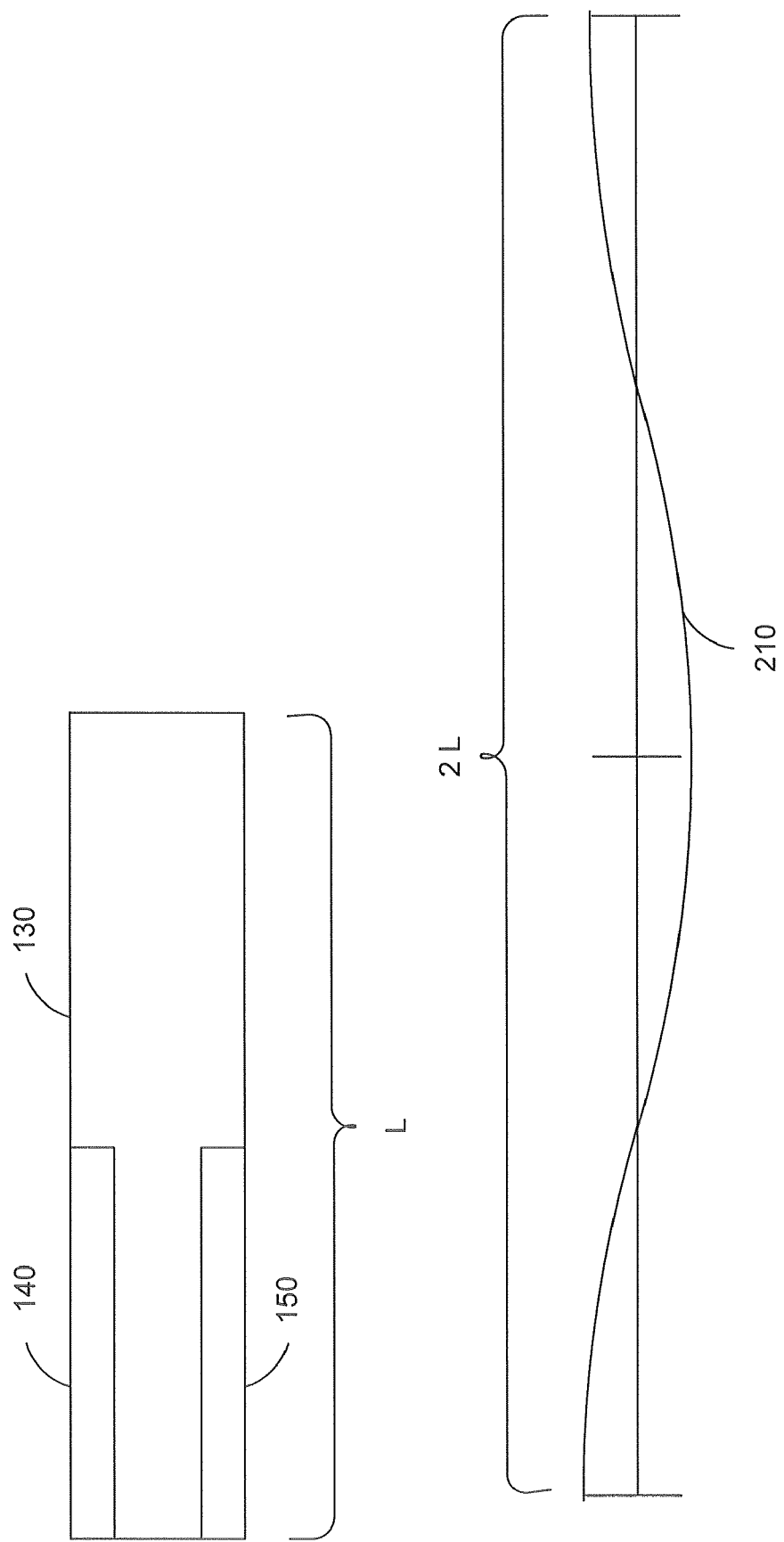
FIG. 2 illustrates an exemplary sound wavelength that is double the length of a photoacoustic cell in a photoacoustic gas sensor according to this disclosure.

FIG. 2 illustrates an exemplary sound wavelength 210 that is double the length of a photoacoustic cell 130 in a photoacoustic gas sensor according to this disclosure. In the photoacoustic cell 130, there are resonances within the photoacoustic cell 130 for certain frequencies. For example, there is a resonance if the wavelength of the sound is double the length of the photoacoustic cell 130. As shown in FIG. 2, the sound wavelength 210 (the length of which is designated 2 L) is double the length (designated L) of the photoacoustic gas sensor 130. The wavelength 2 L corresponds to a resonance frequency within the photoacoustic cell 130. The sound wave is excited by illuminating one half of the photoacoustic cell 130 with modulated light. The other half of the photoacoustic cell 130 remains dark. Times of illumination correspond to a pressure increase in the illuminated half. The pressure decreases when the light is OFF or is weaker.

A resonance frequency within a gas mixture may be used to determine the speed of sound within the gas mixture. In general, frequency is equal to the speed of sound divided by the wavelength, which can be expressed as:

$$\text{Frequency} = (\text{Speed of sound})/(\text{Wavelength}). \qquad (1)$$

A frequency for a particular wave pattern is proportional to the speed of sound. In the case of a cylindrical photoacoustic cell with the one pressure node at the symmetry plane 195 of the cell 130, the lowest resonance frequency "f" is equal to one-half the speed of sound divided by the length of the photoacoustic cell. This may be seen by referring to FIG. 2. The lowest resonance frequency "f" equals the speed of sound divided by the wavelength 2 L, where L represents the length of the photoacoustic cell 130. In this example, the lowest resonance frequency "f" can be expressed as:

$$f = (\tfrac{1}{2} L) \times (\text{speed of sound}). \qquad (2)$$

For structures other than a cylindrical photoacoustic cell, the general relationship that the frequency equals the speed of sound divided by the wavelength still holds. The relationship between a particular physical form of the photoacoustic cell and the wavelength can be determined in any suitable manner. Also, the relationship is a proportional one, meaning the wavelength is proportional to a cell dimension scaling factor. The speed of sound through a gas mixture may be determined from a known value of the resonance frequency and a known value of the cell dimension scaling factor (such as ½ L for a cylindrical photoacoustic cell).

One can use the absorption by a first component of a gas mixture to find the speed of sound in the gas mixture using the resonance frequencies. The principle on which photoacoustic sensor cells operate is the absorption of light energy by certain molecules. By colliding with a second molecule, the absorbed energy in a first molecule is partially transformed into translational energy (which is energy that is related to travel in a straight line) of the first molecule and the second molecule. The higher speeds of the molecules increase the pressure in the illuminated parts of the photoacoustic sensor cell. If the pressure increases and the following gas cooling (during a dark phase) have a similar frequency as a standing wave in the photoacoustic sensor cell and the illuminated part of the cell corresponds more to one anti-node than to others, the standing wave is excited, and the pressure changes at the walls of the photoacoustic sensor cell can become measurable. By adjusting the modulation frequency of light and dark to a maximum response of the standing wave (resonance), the frequency of the unexcited standing wave can be determined. As previously mentioned, the speed of sound can then be determined from the resonance frequency and a cell dimension scaling factor that is proportional to the wavelength.

If the speed of sound in a gas mixture changes, the resonance frequencies in the gas mixture change proportionally. Assume that the concentration of a first gas component in a gas mixture has been determined. If it is then necessary to determine the concentration of a second gas component in the gas mixture, it is possible to use the absorption of the first gas component to determine the speed of sound through the gas mixture based on the resonances. The speed of sound information and the temperature information of the gas mixture can sometimes provide sufficient information to determine the concentration of the second gas component. This technique is then capable of determining the concentration of the second gas component without using a second light source.

The concentration of the second gas component of the gas mixture could be determined from the speed of sound information and from the temperature information in the following manner. For ideal gases that comprise molecules of mass "m" at low pressure, the speed of sound can be expressed as:

$$\text{Speed of sound} = \sqrt{f(c1, c2, \ldots, T)kT} \qquad (3)$$

The letter k represents the Boltzmann constant, the letter T represents the absolute temperature of the gas mixture in Kelvins, and $f(c1, c2, \ldots, T)$ represents a function of T and the gas composition with the different gas concentrations c1, c2, etc. For a pure gas, $f(c1=1, c2=0, T)$ is the ratio $\gamma/m$ where $\gamma$ (gamma) represents a ratio of gas heat capacity at constant pressure to gas heat capacity at constant volume (also known as the adiabatic index), and m represents a mass of a single molecule of the second gas component in kilograms.

For a gas mixture, the function $f(c1, c2, \ldots, T)$ depends upon the composition of the gas and slightly on the temperature. For many mixtures with two gas components and a known balance gas, the function can be reversed. With the value of the function f, the temperature and the concentration of one component known, the concentration of the second component can be calculated. The function $f(c1, c2, \ldots, T)$ needs to be determined only once, by experiment or theory, and then stored in the memory of the controller 190, before the beginning of the gas sensing.

It should be added that in some situations, a determination of the second component is not possible with any precision. An example is a mixture of methane ($CH_4$) and carbon monoxide (CO) with dry air as a balance gas. The methane concentration could be determined by the light absorption in the photoacoustic cell, but carbon monoxide and dry air has essentially the same ratio of ($\gamma/m$), and the carbon monoxide concentration could not be determined by measuring the speed of sound.

Figure 3:
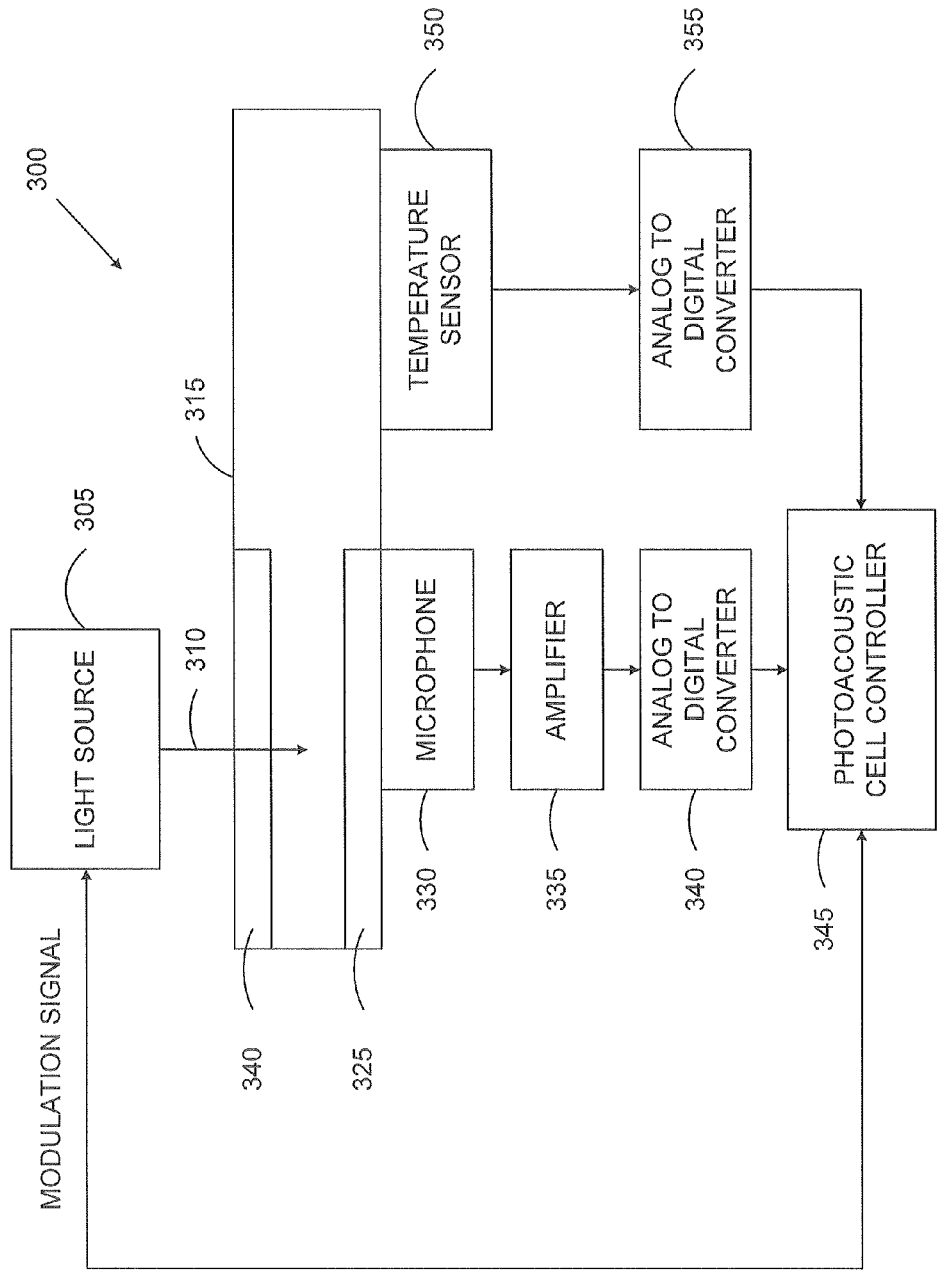
FIG. 3 illustrates an example photoacoustic gas sensor according to this disclosure.

FIG. 3 illustrates an exemplary photoacoustic gas sensor 300 according to this disclosure. A light source 305 generates light 310 of a certain wavelength or wavelength range, most often in the infrared (IR) range, and with a certain modulation. The light 310 enters a portion of the photoacoustic cell 315 (also referred to as a photoacoustic gas sensor chamber 315) of the photoacoustic gas sensor 300 through a transparent or translucent wall 340. The opposite wall of the photoacoustic cell 315 comprises an opaque wall 325 or mirror 325. Note that while the photoacoustic cell 315 is shown here as being cylindrical, the photoacoustic cell 315 could have any other suitable shape (such as spherical). The photoacoustic cell 315 generally includes any suitable photoacoustic cell structure.

A microphone 330 is associated with and in acoustic contact with the photoacoustic cell 315. The microphone 330 is best located far away from the pressure nodes of the standing wave that should be excited. The microphone 330 includes any suitable structure for capturing audio information associated with the operation of the gas sensor 300. The output of the microphone 330 is provided to an amplifier 335, which amplifies the output signal of the microphone 330. The amplifier 335 includes any suitable structure for amplifying audio signals. The amplifier 335 might provide the amplified output to an analog-to-digital converter 340, which converts the amplified analog signal to a digital signal, or the amplifier 335 might use the modulation signal of the light in an analog way, as a lock-in or similar method. The analog-to-digital converter 340 includes any suitable structure for converting one or more analog signals into one or more corresponding digital signals. The analog-to-digital converter 340 provides the digital signal to a photoacoustic cell controller 345. The photoacoustic cell controller 345 uses the digital signal to determine the concentration level of one or more gas components that are in the mixture of gases within the photoacoustic cell 315. The controller 345 includes any suitable structure for calculating concentration levels of gas components, such as a microprocessor, microcontroller, digital signal processor (DSP), field programmable gate array (FPGA), or application-specific integrated circuit (ASIC).

As shown in FIG. 3, the photoacoustic gas sensor 300 also includes a temperature sensor 350 and an analog-to-digital converter 355. The temperature sensor 350 is associated with and may be in contact with the photoacoustic cell 315. The temperature sensor 350 senses the temperature of the mixture of gases within the photoacoustic cell 315. The temperature sensor 350 provides an analog signal that represents the temperature to the analog-to-digital converter 355, which converts the analog temperature signal to a digital temperature signal and provides the digital temperature signal to the photoacoustic cell controller 345.

As also shown in FIG. 3, an output of the photoacoustic cell controller 345 is connected to an input of the light source 305. As described in more detail below, the photoacoustic cell controller 345 is capable of sending a control signal to the light source 305 to lock the modulation frequency of the light source 305 to a good resonance.

If the concentration of a first gas component has been measured (by the controller 345) and if a good resonance lies within an accessible region for the frequency of the light modulation, it may be possible to obtain a measure of the speed of sound in the gas mixture within the photoacoustic cell 315. The second condition (a good resonance that is accessible) has typically not been achievable in the past. This is because, for photoacoustic cells of 1 cm diameter or less, the resonances are typically around 20 kHz or greater. This is far beyond the reach of previously-used light sources, such as light bulbs. However, it is now possible to access suitable frequencies at reasonable costs using novel light sources, such as light emitting diodes (LEDs) with quantum dots (although other suitable light sources could be used).

Locking the modulation frequency of the light source 305 to a good resonance may involve the use of an adjustable frequency for the light modulation. In this example, the photoacoustic cell controller 345 is capable of changing the frequency of the light modulation of light source 305 depending upon the photoacoustic response that the photoacoustic cell controller 345 detects.

Figure 4:
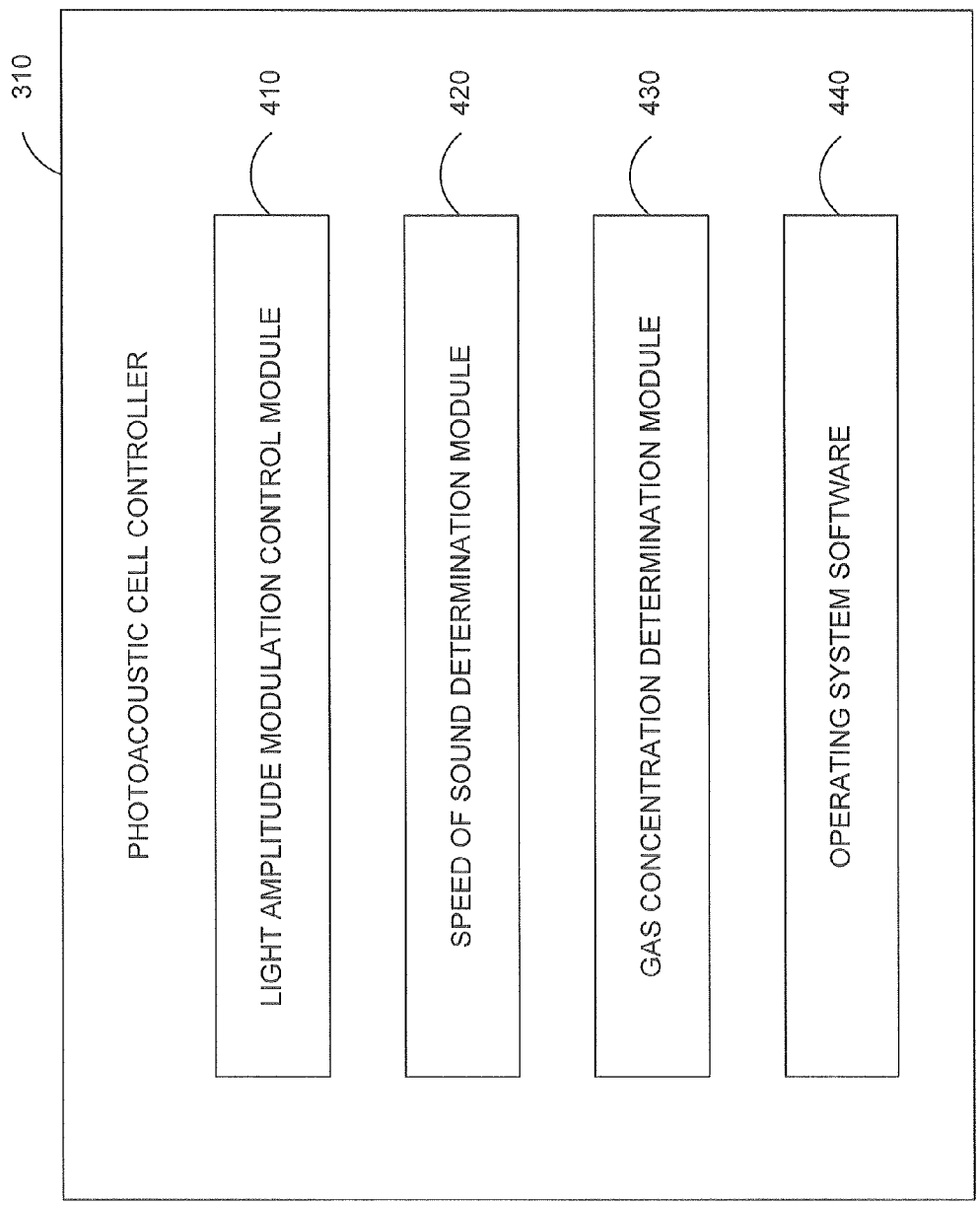
FIG. 4 illustrates an example photoacoustic cell controller according to this disclosure.

FIG. 4 illustrates an example photoacoustic cell controller 345 according to this disclosure. In this example, the photoacoustic cell controller 345 includes a light amplitude modulation control module 410, a speed of sound determination module 420, a gas concentration determination module 430, and operating system software 440. In this particular example, the photoacoustic cell controller 345 is implemented using computer hardware and computer software instructions that cooperate and work together to carry out the operations of the photoacoustic cell controller 345. Of course, other embodiments of the photoacoustic cell controller 345 could also be used.

The light amplitude modulation control module 410 controls the modulation of the light amplitude. Using the light amplitude control module 410, the photoacoustic cell controller 345 sends a control signal to the light source 305 to lock the modulation frequency of the light source 305 to a good resonance.

The speed of sound determination module 420 determines the speed of sound through the gas mixture in the photoacoustic cell 315. Using the speed of sound determination module 420, the photoacoustic cell controller 345 determines the speed of sound through the gas mixture using a known value of the resonance frequency and a known value of the cell dimension scaling factor for the photoacoustic cell 315.

The gas concentration determination module 430 determines the gas concentration of a second gas component in the gas mixture in the photoacoustic cell 315. Using the value of the speed of sound provided by the speed of sound determination module 420 and the temperature of the photoacoustic cell 315 provided by the temperature sensor 350, the photoacoustic cell controller 345 determines the gas concentration of the second gas component of the gas mixture using Equation (3) and the predetermined function f(c1, c2, . . . , T).

The photoacoustic gas sensor 300 can use a photoacoustic cell 315 best with a mode that has a sharp resonance, corresponding to a low damping of the standing wave. The resonances of radial oscillations may usually be sharper than those of longitudinal oscillations, and the light 310 from the light source 305 may be focused so as to generate the desired oscillations. As noted above, the photoacoustic cell controller 345 can also change the frequency of the light modulation depending upon the measured photoacoustic response, allowing the photoacoustic cell controller 345 to send a control signal to the light source 305 to lock onto a desired resonance frequency. In addition, the temperature sensor 350 could have sufficient stability and sensitivity of ⅒ of a degree Kelvin (0.1K°). This may be needed since an increase in temperature of ½ of a degree Kelvin (0.5K°) can increase the resonance frequency by 0.09% in air.

Figure 5:
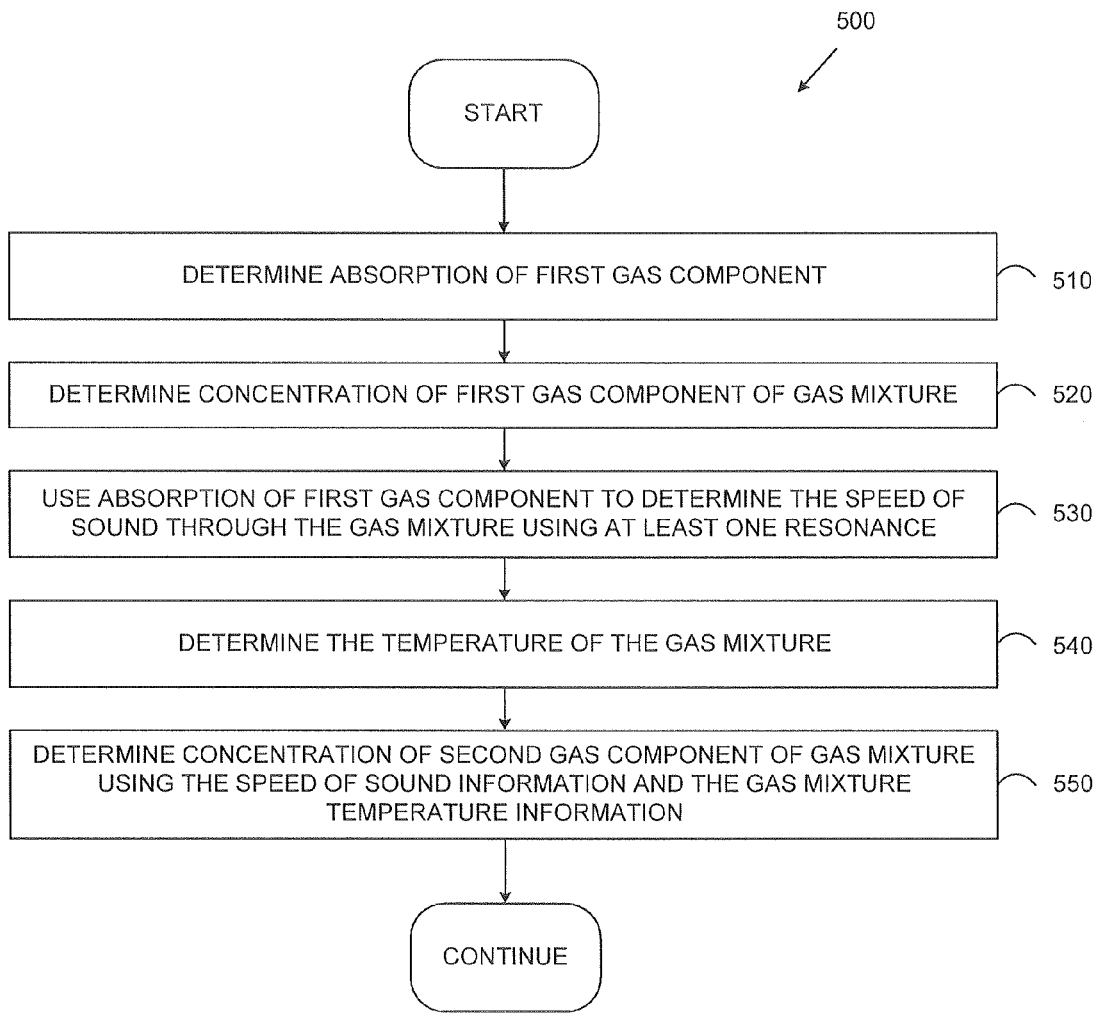
FIG. 5 illustrates an example method for using the speed of sound in photoacoustic gas sensor measurements according to this disclosure.

FIG. 5 illustrates an example method for using the speed of sound in photoacoustic gas sensor measurements according to this disclosure. The photoacoustic gas controller 300 determines the absorption of the first gas component at step 510. The photoacoustic gas sensor 300 determines the concentration of a first gas component of a gas mixture within a photoacoustic cell 315 at step 520.

The photoacoustic gas sensor 300 uses the absorption of the first gas component to determine the speed of sound through the gas mixture using at least one resonance of the photoacoustic cell 315 at step 530. The photoacoustic gas sensor 300 determines the temperature of the gas mixture in the photoacoustic cell 315 using a temperature sensor 350 at step 540. The photoacoustic gas sensor 300 determines a concentration of a second gas component of the gas mixture within the photoacoustic cell 315 using the speed of sound information and the gas mixture temperature information at step 550. At this point, the concentration(s) of the gas component(s) can be used in any suitable manner. For instance, the concentrations can be stored for later use and/or output from the photoacoustic gas sensor 300. As a particular example, one or more of the concentrations can be output to a component for determining whether to generate an alarm based on the measured concentration(s).

The photoacoustic gas sensor 300 described above operates in a different manner than conventional photoacoustic gas sensors. For example, it has been suggested that one should avoid operating photoacoustic gas sensors near resonance frequencies. This is supposedly because both the signal and noise that is generated near resonance frequencies is maximal there, and locking in the resonance frequency may be necessary. It may be noted that noise from gas flows can be reduced or minimized (such as by temporarily closing off the photoacoustic cell 315) during the measurement process. Noise from other sources may not depend on the resonance conditions. Also, it has become cheaper to lock in the modulation frequency of a light source to a resonance frequency and to measure close to and far away from a resonance frequency (either simultaneously or alternately).

The photoacoustic gas sensor 300 could be used in a wide variety of applications. For example, the photoacoustic gas sensor 300 may be used to control air ventilation in buildings, such as to measure carbon dioxide ($CO_2$) concentrations. Also, humidity is an important parameter in establishing a comfortable environment. An increase of humidity from 50% to 60% may increase the resonance frequencies in a photoacoustic cell 315 by about 0.04% (or 8 Hz for a 20 kHz resonance). Such a frequency increase can be easily measurable using the photoacoustic gas sensor 300 (assuming the noise of the measurement is adequately overcome).

The photoacoustic gas sensor 300 may further be used to determine the composition of natural gas. Natural gas is a mixture of methane, carbon dioxide, higher hydrocarbons, and other gases. Methane and carbon dioxide both absorb in the infrared. The speed of sound of a natural gas mixture is therefore accessible and can provide important information about the composition of the mixture of gases in the natural gas.

While FIGS. 2 through 5 have illustrated various features of example embodiments for the present invention, various changes may be made to the figures. For example, any suitable light wavelengths having associated resonances could be used in a photoacoustic gas sensor. Also, various components of the photoacoustic gas sensor 300 could be combined, omitted, or further subdivided and additional components could be added according to particular needs. The same is true for the photoacoustic cell controller 345, and each module in the photoacoustic cell controller 345 could be implemented using any suitable hardware, software, firmware, or combination thereof. In addition, while shown as a series of steps, various steps in FIG. 5 could overlap, occur in parallel, occur multiple times, or occur in a different order.

It may be advantageous to set forth definitions of certain words and phrases used throughout this patent document. The term "couple" and its derivatives refer to any direct or indirect communication between two or more elements, whether or not those elements are in physical contact with one another. The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. The term "controller" means any device, system, or part thereof that controls at least one operation. A controller may be implemented in hardware, firmware, software, or some combination of at least two of the same. The functionality associated with any particular controller may be centralized or distributed, whether locally or remotely.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of the invention, as defined by the following claims.

What is claimed is:

1. A photoacoustic gas sensor comprising:
a photoacoustic cell configured to receive a gas mixture;
a light source configured to provide modulated light to the photoacoustic cell which is absorbed by a first gas component in the gas mixture; and
a photoacoustic cell controller configured to:
calculate pressure variations resulting from the light absorption;
determine a speed of sound through the gas mixture based on the light absorption; and
determine a concentration of a second gas component in the gas mixture using a concentration of the first gas component and the speed of sound, wherein the concentration of the first gas component is previously determined.

2. The photoacoustic gas sensor of claim 1, wherein:
the gas mixture further comprises a third gas component for balance; and
the photoacoustic cell controller is further configured to determine the concentration of the first gas component using the pressure variations prior to determining the concentration of the second gas component.

3. The photoacoustic gas sensor of claim 1, wherein the photoacoustic cell controller is further configured to determine the speed of sound through the gas mixture using at least one resonance of the photoacoustic cell.

4. The photoacoustic gas sensor of claim 3, wherein the photoacoustic cell controller is configured to determine the speed of sound using a relationship between a resonance frequency of the photoacoustic cell and a wavelength or wavelength range of the light.

5. The photoacoustic gas sensor of claim 1, further comprising:
a temperature sensor configured to measure a temperature of the gas mixture;
wherein the photoacoustic cell controller is configured to determine the concentration of the second gas component in the gas mixture using the speed of sound, the temperature, and the concentration of the first gas component.

6. The photoacoustic gas sensor of claim 5, wherein the photoacoustic cell controller is configured to determine the concentration of the second gas component in the gas mixture using a relationship of:

$$\text{Speed of sound} = \sqrt{f(c1, c2, \ldots, T)kT}$$

where k represents the Boltzmann constant, T represents an absolute temperature of the gas mixture in Kelvins, and $f(c1, c2, \ldots, T)$ is a predetermined function of T and a composition of the gas mixture with different concentrations ($c1, c2, \ldots$).

7. The photoacoustic gas sensor of claim 1, wherein the photoacoustic cell controller is further configured to control the light source in order to lock a frequency of the light to a resonance associated with the photoacoustic cell.

8. The photoacoustic gas sensor of claim 1, wherein:
the light has a first wavelength or wavelength range and is absorbed by the first gas component; and
the photoacoustic cell controller is configured to determine the concentration of the second gas component without any measurements taken using light having a second wavelength or wavelength range that is absorbed by the second gas component.

9. A photoacoustic cell controller comprising:
a speed of sound determination module configured to determine a speed of sound through a gas mixture in a photoacoustic cell using an absorption of a first gas component in the gas mixture; and
a gas concentration determination module configured to determine a concentration of a second gas component using the speed of sound through the gas mixture and a concentration of the first gas component, wherein the concentration of the first gas component is previously determined.

10. The photoacoustic cell controller of claim 9, further comprising:
a light frequency modulation control module configured to control a light source to lock a light frequency to a resonance, the light source configured to provide light to the photoacoustic cell.

11. The photoacoustic cell controller of claim 10, wherein the speed of sound determination module is configured to determine the speed of sound through the gas mixture using at least one resonance of the photoacoustic cell.

12. The photoacoustic cell controller of claim 10, wherein the gas concentration determination module is further configured to calculate pressure variations resulting from the absorption and to determine the concentration of the first gas component using the pressure variations prior to determining the concentration of the second gas component.

13. The photoacoustic cell controller of claim 9, wherein the speed of sound determination module is configured to determine the speed of sound through the gas mixture using a relationship between a resonance frequency of the photoacoustic cell and a wavelength or wavelength range of light provided to the photoacoustic cell.

14. The photoacoustic cell controller of claim 9, wherein the gas concentration determination module is configured to determine the concentration of the second gas component using the speed of sound through the gas mixture and a temperature of the gas mixture.

15. The photoacoustic cell controller of claim 14, wherein the gas concentration determination module is configured to determine the concentration of the second gas component using a relationship of:

$$\text{Speed of sound} = \sqrt{f(c1, c2, \ldots, T)kT}$$

where k represents the Boltzmann constant, T represents an absolute temperature of the gas mixture in Kelvins, and $f(c1, c2, \ldots, T)$ is a predetermined function of T and a composition of the gas mixture with different concentrations ($c1, c2, \ldots$).

16. The photoacoustic cell controller of claim 9, wherein:
the gas concentration determination module is further configured to determine the concentration of the first gas component based on measurements taken using light having a first wavelength or wavelength range that is absorbed by the first gas component prior to determining the concentration of the second gas component; and the gas concentration determination module is configured to determine the concentration of the second gas component without any measurements taken using light having a second wavelength or wavelength range that is absorbed by the second gas component.

17. A method of operating a photoacoustic gas sensor that comprises a photoacoustic cell, the method comprising:
determining a speed of sound through a gas mixture in the photoacoustic cell using an absorption of a first gas component in the gas mixture; and
determining a concentration of at least one other gas component of the gas mixture using the speed of sound through the gas mixture and a concentration of the first gas component, wherein the concentration of the first gas component is previously determined.

18. The method of claim 17, further comprising:
placing the gas mixture within the photoacoustic cell, wherein the gas mixture comprises the first gas component, the second gas component, and a third gas component for balance;
calculating pressure variations resulting from the absorption; and
determining a concentration of the first gas component using the pressure variations prior to determining the concentration of the second gas component.

19. The method of claim 17, further comprising:
controlling a light source that provides light to the photoacoustic cell in order to lock a light frequency to a resonance.

20. The method of claim 17, wherein determining the speed of sound through the gas mixture comprises:
determining the speed of sound through the gas mixture using the absorption and at least one resonance of the photoacoustic cell.

21. The method of claim 17, further comprising:
measuring a temperature of the gas mixture;
wherein determining the concentration of the second gas component comprises determining the concentration of the second gas component using the speed of sound through the gas mixture and the temperature.

* * * * *